United States Patent
Steadman Booker et al.

(10) Patent No.: US 11,988,785 B2
(45) Date of Patent: May 21, 2024

(54) CHARGE SHARING COMPENSATION WITH SAMPLED DISCRIMINATORS

(71) Applicant: KONINKLIJKE PHILIPS N.V., Eindhoven (NL)

(72) Inventors: Roger Steadman Booker, Aachen (DE); Christoph Herrmann, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 430 days.

(21) Appl. No.: 17/436,093

(22) PCT Filed: Mar. 4, 2020

(86) PCT No.: PCT/EP2020/055616
§ 371 (c)(1),
(2) Date: Sep. 3, 2021

(87) PCT Pub. No.: WO2020/182555
PCT Pub. Date: Sep. 17, 2020

(65) Prior Publication Data
US 2022/0187477 A1    Jun. 16, 2022

(30) Foreign Application Priority Data
Mar. 14, 2019 (EP) .................... 19162839

(51) Int. Cl.
*G01T 1/17* (2006.01)
*A61B 6/00* (2006.01)
*A61B 6/42* (2024.01)

(52) U.S. Cl.
CPC ............ *G01T 1/171* (2013.01); *A61B 6/4241* (2013.01)

(58) Field of Classification Search
None
See application file for complete search history.

(56) References Cited

U.S. PATENT DOCUMENTS

| | | | |
|---|---|---|---|
| 7,868,665 B2 * | 1/2011 | Tumer | G01T 1/171 327/51 |
| 8,945,221 B2 | 2/2015 | Barrett | |

(Continued)

FOREIGN PATENT DOCUMENTS

| | | |
|---|---|---|
| WO | WO2008146230 A2 | 12/2008 |
| WO | WO2008146230 A3 | 12/2008 |
| WO | WO2016096622 A1 | 6/2016 |

OTHER PUBLICATIONS

PCT International Search Report, International application No. PCT/EP2020/055616, dated Apr. 30, 2020.

(Continued)

*Primary Examiner* — Thomas R Artman
(74) *Attorney, Agent, or Firm* — Larry Liberchuk

(57) ABSTRACT

The present invention relates to photon counting. In particular, a photon-counting data acquisition module is provided. The photon-counting data acquisition module comprises a signal input unit and one or more data acquisition channels, each channel adapted for converting at least one train of pulses received from the signal input unit to a counter signal. Each data acquisition channel comprises a pulse maximum identifier and a discriminator/counter pair comprising a discriminator and a counter. The pulse maximum identifier is configured to identify a maximum of a pulse in the at least one received train of pulses. The discriminator is configured to be triggered, by a detection of a maximum of a pulse in the at least one received train of pulses, to compare the pulse with at least one signal threshold to generate the counter signal. Alternatively, the counter is configured to be enabled in response to a detection of a maximum of a pulse to generate the counter signal.

9 Claims, 8 Drawing Sheets

(56) References Cited

U.S. PATENT DOCUMENTS

| | | | |
|---|---|---|---|
| 9,081,103 B2* | 7/2015 | Loeliger | G01T 1/171 |
| 9,599,730 B2* | 3/2017 | Spahn | G01T 1/247 |
| 10,054,692 B2* | 8/2018 | Roessl | G01T 1/241 |
| 10,365,380 B2* | 7/2019 | Steadman Booker | G01T 1/2928 |
| 10,422,887 B2* | 9/2019 | Persson | G01T 1/17 |
| 10,809,396 B2 | 10/2020 | Blevis | |
| 11,002,861 B2* | 5/2021 | Persson | G01T 1/247 |
| 11,002,865 B2 | 5/2021 | Roessl | |
| 11,178,346 B2* | 11/2021 | Steadman Booker | G01T 1/2928 |
| 2004/0017224 A1* | 1/2004 | Tumer | H03F 3/087 327/51 |
| 2013/0044248 A1* | 2/2013 | Tumer | H03F 3/087 348/E5.091 |
| 2014/0175299 A1* | 6/2014 | Spahn | G01T 1/247 250/394 |
| 2014/0191136 A1* | 7/2014 | Loeliger | G01T 1/171 250/394 |
| 2017/0357013 A1* | 12/2017 | Roessl | G01T 1/28 |
| 2018/0196149 A1* | 7/2018 | Blevis | G01T 1/243 |
| 2018/0292544 A1* | 10/2018 | Persson | G01T 1/17 |
| 2018/0329086 A1 | 11/2018 | Roessl | |
| 2019/0025440 A1* | 1/2019 | Steadman Booker | G01T 1/2928 |
| 2019/0204456 A1* | 7/2019 | Persson | G01T 1/247 |
| 2021/0067710 A1* | 3/2021 | Steadman Booker | G01T 1/2928 |
| 2022/0187477 A1* | 6/2022 | Steadman Booker | G01T 1/171 |
| 2022/0187478 A1* | 6/2022 | Hsieh | A61B 6/4241 |

OTHER PUBLICATIONS

Llopart X. et al., "Medipix2—a 64k Pixel Read Out Chip with 55 μm Square Elements Working in Single Photon Counting Mode", 2001 IEEE Nuclear Science Symposium Conference Record, vol. 49, issue 5, p. 2279-2283.

Bochenek M. et al., "IBEX—Versatile Readout ASIC with Spectral Imaging Capability and High Count Rate Capability", IEEE RJTransactions on Nuclear Science, vol. 65, No. 6, pp. 1285-1291, Jun. 2018.

Ullberg C. et al., "Photon Counting, Dual Energy X-Ray Imaging at CT Count Rates—Measurements and Implications of In-Pixel Charge Sharing Correction", SPIE Physics of Medical Imaging, vol. 10573, 2018.

* cited by examiner

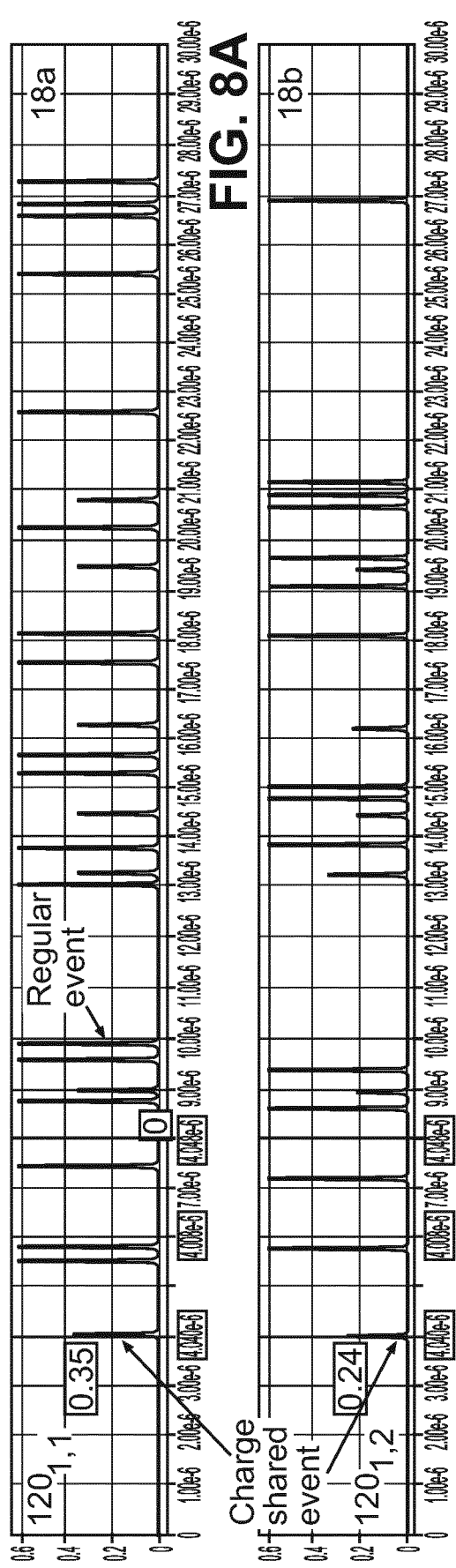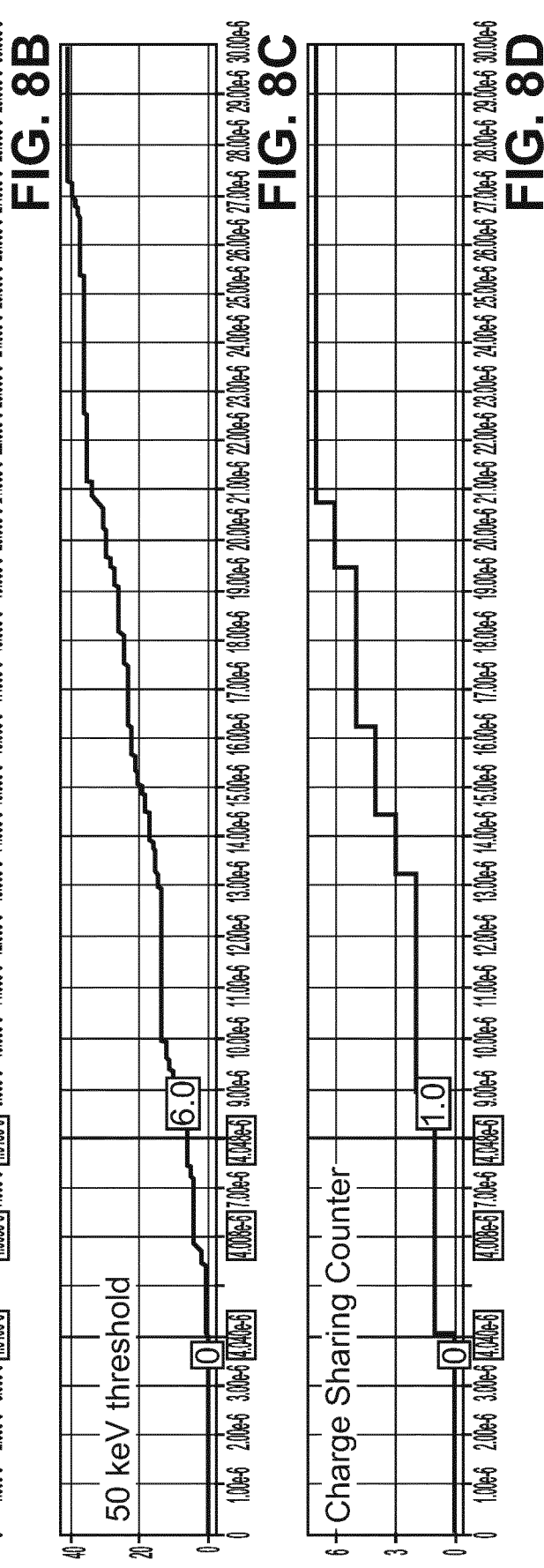

CHARGE SHARING COMPENSATION WITH SAMPLED DISCRIMINATORS

FIELD OF THE INVENTION

The present invention relates to photon counting. In particular, the present invention relates to a photon-counting data acquisition module, a pixelated photon-counting detector, a method for photon counting, as well as a computer program element and a computer readable medium.

BACKGROUND OF THE INVENTION

Photon counting detectors capable of discriminating photon energies, such as X-ray photon energies, have been developed in past decades for various applications e.g. in medical imaging and material science. Photon counting detectors are operated in a pulse mode based on single event, meaning that theoretically each interaction occurred within the detection material can be processed and registered individually.

Photon counting data acquisition modules have been developed to convert an energy of photons to a count signal indicative of the number of photons having an energy above a threshold. For example, US 2018/0329086 A1 describes a photon counting data acquisition module in form of a read-out Application Specific Integrated Circuit (ASIC) for an X-ray detector with pixels being clustered using an anti-charge-sharing grid.

In photon counting, two or more nearly simultaneously incident photons may be regarded as a single event with a higher energy, resulting in not only dead time losses, but also a distortion of the recorded pulse height spectrum. Due to pile-up effect and dead time loss, the linearity between the detected photon rate and the incident photon rate gradually lacks with increased photon fluxes. If the dead time extends by the following event arrived within its dead time, ambiguity may exist between observed count rate and incident count rate. This count rate performance is also referred to as paralyzable.

WO 2008/146230A2 describes a photon rate counter including a radiation detector and signal conditioning circuitry. The photon rate counter produces a count value indicative of a total number of photons received by a detector. One or more photon counters produce count values indicative of photons having varying energy characteristics. The counters disregard pileup pulses.

WO 2016/096622 A1 relates to a detector for detecting ionizing radiation, comprising a directly converting semiconductor layer for producing charge carriers in response to incident ionizing radiation and a plurality of electrodes corresponding to pixels for registering the charge carriers and generate a signal corresponding to registered charge carriers, wherein an electrode of the plurality of electrodes is structured to two-dimensionally intertwine with at least two adjacent electrodes to register the charge carriers by said electrode and by at least one adjacent electrode.

SUMMARY OF THE INVENTION

There may be a need to provide a non-paralyzable photon-counting data acquisition device.

The object of the present invention is solved by the subject-matter of the independent claims, wherein further embodiments are incorporated in the dependent claims. It should be noted that the following described aspects of the invention apply also for the photon-counting data acquisition module, the pixelated photon-counting detector, the method for photon counting, as well as the computer program element and the computer readable medium.

A first aspect of the present invention relates to a photon-counting data acquisition module. The photon-counting data acquisition module comprises a signal input unit and one or more data acquisition channels, each channel adapted for converting at least one train of pulses received from the signal input unit to a counter signal. Each data acquisition channel comprises a pulse maximum identifier and a discriminator/counter pair comprising a discriminator and a counter. The pulse maximum identifier is configured to identify a maximum of a pulse in the at least one received train of pulses. The discriminator is configured to be triggered, by a detection of a maximum of a pulse in the at least one received train of pulses, to compare the pulse with at least one signal threshold to generate the counter signal. Alternatively, the counter is configured to be enabled in response to the detection of a maximum of a pulse in the at least one received train of pulses to generate the counter signal.

Since the discriminator/counter pair is allowed to evaluate signals only in discrete time intervals, the system is inherently non-paralyzable in the sense that the observed count rate increases monotonically with the input count rate. In an example, the discriminator may be time-discrete discriminator, which can be triggered, by a detection of a maximum of a pulse, to compare the pulse with the at least one signal threshold. Alternatively, the discriminator could be time continued but it is only allowed to increment the associated counter when enabled. In other words, the discriminator operates normally, and the time-discrete component is accomplished by digitally enabling/disabling the counting function. In particular, if a local maximum is detected (e.g. during pile-up), the next local maximum will again be detected, and the discriminator is evaluated. Thus, incrementing the counters in high pile-up situations is governed by the detection of local maxima. There may be some randomization of the output count rate, and issues of the multi-energy case may be circumvented. A non-paralyzable count rate behavior may be considered advantageous, since there is no ambiguity between observed count rate and incident count rate as in the paralyzable case.

The photon-counting data acquisition module may be connected to various photodetectors including, but not limited to, photomultiplier, geiger counter, single-photon avalanche diode, superconducting nanowire single-photon detector, transition edge sensor, charge-coupled device or scintillation counter. A various spectral range may be covered, from near-infrared and ultraviolet wavelengths to high-energy regions, such as X-ray and gamma ray, for different applications such as chemical analysis, medical imaging and laser measurement. The photon-counting data acquisition module may be part of, or include an ASIC, an electronic circuit, a processor and/or memory that execute one or more software or firmware programs, a combinational logical circuit, and/or other suitable components that provide the described functionality. For example, the photon-counting data acquisition module may be a read-out ASIC for a photon-counting Computed Tomography (CT) detector.

The pulse maximum identifier may comprise a zero-crossing threshold preceded by a differentiator. A possible implementation of the pulse maximum identifier is illustrated in FIG. 4.

The discriminator may include one or more comparators. Each comparator compares the amplitude of the pulse with one or more predetermined energy thresholds that correspond to one or more different energy ranges. This may be triggered by a detection of a maximum of a pulse in the at least one received train of pulses. Alternatively, the counter may be enabled in response to the detection of a maximum of a pulse. Thus, the input of each comparator is only evaluated when input signal in form of a train of pulses has reached a local maximum. The benefit may be the resulting non-paralyzable count rate behavior. The comparators may respectively produce output signals indicative of whether the energy of a detected photon event is above or below a threshold. A counter counts, for each energy range, a number of pulses that falls within the energy range based on the comparator output signals.

According to an embodiment of the present invention, each data acquisition channel is adapted for being connected to a pixel of a pixelated photon-counting detector to receive a train of pulses indicative of an energy of photons incident on the pixel, or to a cluster of sub-pixels of a pixelated photon-counting detector to receive a plurality of trains of pulses, each indicative of an energy of photons incident on a respective sub-pixel of the cluster.

The pixelated photon-counting detector may be a detector for e.g. X-ray, gamma ray, or fluorescence imaging. In an example, the photon-counting data acquisition module may be connected to a pixelated detector without sub-pixelation, such as Philips proprietary ChromAIX2, which has pixels of a pitch of about 500 μm. In another example, the photon-counting data acquisition module may be connected to a pixelated detector with sub-pixelation. In this case, each data acquisition channel may be linked to an analog front-end for dealing with sub-pixels and implement charge-sharing corrections, as will be explained hereafter and particularly with respect to the exemplary embodiment in FIG. 3.

According to the first aspect of the present invention, the at least one train of pulses received from the signal input unit comprises a first train of pulses and a second train of pulses. The data acquisition channel further comprises a selection logic. The pulse maximum identifier is configured to identify maxima of a first pulse in the first train of pulses and a second pulse in the second train of pulses. The selection logic is configured to determine whether the maxima of the first pulse and the second pulse are within a coincidence window and to enable the discriminator to evaluate the first pulse in the first train of pulses or the second pulse in the second train of pulses directly if the first and second pulses are not within the coincidence window, or a sum of the first and second pulses if the first and second pulses are within the coincidence window.

The at least one train of pulses may further comprise a third train of pulses, a fourth train of pulses, etc. In other words, the following discussion is also scalable to a large number of trains of pulses. The selection logic may determine whether a given event, i.e. a pulse indicative of an energy incident on one or more sub-pixels, is confined to a single sub-pixel or charge shared across one or more neighbors. The input to the thresholds, i.e. the energy discriminator, is dependent on the decision. That is, for every single photon, a decision is made to feedthrough the shaper directly to the discriminator or to take the signal from a shaper summing mode which is continuously available.

This may allow charge sharing compensation, while avoiding a degradation of count rate performance and spectral performance. This may be beneficial for smaller pixels, which on the one hand relax the stringent requirement of the photon counting channel, while on the other hand may be severely impaired by the need to correct for charge sharing.

The use of on-the-fly coincidence detection and a time-discrete discriminator circuit or a time-discrete counter may facilitate the path for using smaller pixels, while preserving both count-rate and spectral performance.

According to an embodiment of the present invention, the selection logic comprises i) a coincidence detector, ii) a switch control, and iii) a threshold sampling control. The coincidence detector is configured to evaluate a state of an output of the pulse maximum identifier and to determine whether the first pulse in the first train of pulses, the second pulse in the second train of pulses, or both the first and second pulses are within the coincidence window. The switch control is configured to determine, based on the evaluation and determination of the coincidence detector, whether to feedthrough the first pulse, the second pulse, or a sum of the first and second pulses to an input of the discriminator. The threshold sampling control is configured to evaluate a state of an output of the pulse maximum identifier and to trigger the discriminator to perform comparison based on the evaluated state.

The coincidence detector may represent a logic response to multiple inputs. Examples of the coincidence detector include, but not limited to, a truth table, a combinatorial logic, and a state machine. This will be explained hereafter and particularly with respect to FIG. 3.

According to an embodiment of the present invention, the data acquisition channel further comprises an adder configured to add the first and second train of pulses.

The adder may be an analogue adder. This may be done with an amplifier, e.g. in the voltage domain or in the current domain. In an example, the signals are continuously summed into a single node. In another example, e.g. for a large number of pixels or sub-pixels, it may be advantageous to only add pixels or sub-pixels which are in fact processing a shaper pulse.

According to an embodiment of the present invention, the data acquisition channel further comprises a multiplexer adapted for forwarding the first train of pulses, the second train of pulses, and a sum of the first and second trains of pulses to the discriminator in a time-multiplexed manner.

In other words, the threshold system, i.e. the energy discriminator, may be time-multiplexed across all e.g. sub-pixels. Thus, sub-pixels within a cluster share a set of energy thresholds, i.e. the energy discriminator.

According to an embodiment of the present invention, the discriminator/counter pair further comprises a charge-sharing counter adapted for being triggered by a detection of the maxima of the first pulse and the second pulse within a coincidence window to increase a value.

The charge-sharing counter may be beneficial in determining pile-up corrections.

A second aspect of the present invention relates to a pixelated photon-counting detector. The pixelated photon-counting detector comprises an array of pixels and a photon-counting data acquisition device as described above and below. Each data acquisition channel of the photon-counting data acquisition device is configured to receive a train of pulses indicative of an energy of photons incident on a respective pixel of the pixelated photon-counting detector.

As mentioned above, the pixelated photon-counting detector may exhibit non-paralyzable count rate behavior, which may be advantageous, since there is no ambiguity between observed count rate and incident count rate as in the paralyzable case.

According to an embodiment of the present invention, the pixel is a cluster of sub-pixels. Each data acquisition channel is configured to receive a plurality of pulse trains, each indicative of an energy of photons incident on a respective sub-pixel of the cluster.

As mentioned above, this may facilitate the path for using smaller pixels to relax the stringent requirement of the photon-counting channel, while preserving both count-rate and spectral performance.

According to an embodiment of the present invention, the pixelated photon-counting detector is at least one of an X-ray detector, a gamma ray detector, and a fluorescence detector.

A third aspect of the present invention relates to a method for photon counting. The method comprises identifying, with a pulse maximum identifier, a maximum of a pulse in at least one received train of pulses and triggering a discriminator, by a detection of a maximum of a pulse in the at least one received train of pulses, to compare the pulse with at least one signal threshold. Alternatively, a counter is enabled, in response to a detection of a maximum of a pulse in the at least one received train of pulses, to generate the counter signal.

According to the third aspect of the present invention, the at least one received train of pulses comprises a first train of pulses and a second train of pulses. The method further comprises identifying maxima of a first pulse in the first train of pulses and a second pulse in the second train of pulses, determining whether the maxima of the first pulse and the second pulse are within a coincidence window, and evaluating the first pulse in the first train of pulses, the second pulse in the second train of pulses, or a sum of the first pulse and the second pulse based on the determination result.

According to an embodiment of the present invention, the at least one received train of pulses are indicative of an energy of photons incident on a respective pixel or a respective cluster of sub-pixels of a pixelated photon-counting detector.

A fourth aspect of the present invention relates to a computer program element or computer program product for controlling a photon-counting data acquisition module as described above and below, which, when being executed by a processing unit, is adapted to perform the method steps as described above and below.

A fifth aspect of the present invention relates to a computer readable medium having stored the computer program product or element.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings:

FIGS. 8A-8D shows schematically two train of pulses representing a mixture of single and charge shared events and the corresponding outputs of a discriminator according to some embodiments of the present disclosure.

DETAILED DESCRIPTION OF EMBODIMENTS

Figure 1:
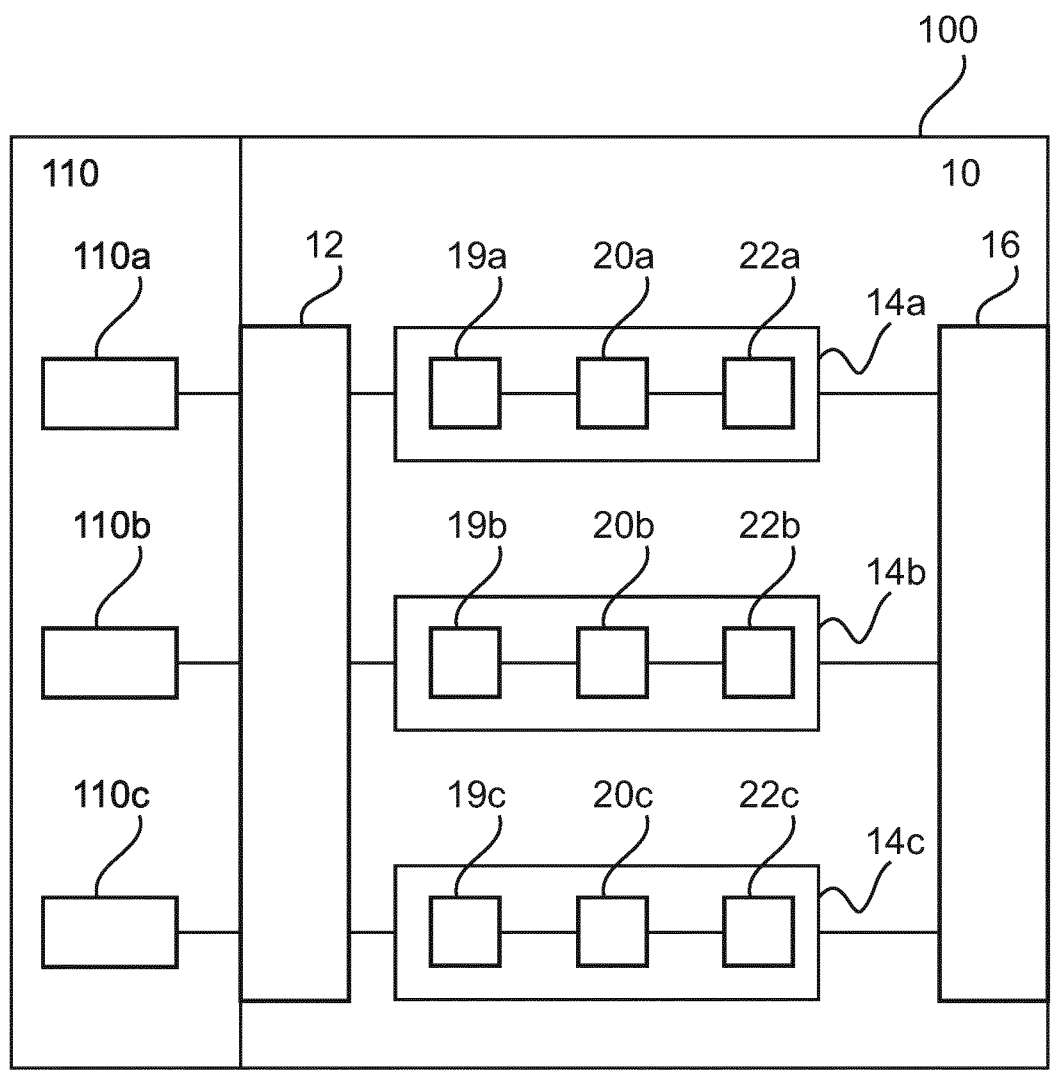
FIG. 1 shows schematically a photon-counting data acquisition module as a part of a pixelated photon-counting detector according to some embodiments of the present disclosure.

FIG. 1 shows a photon-counting data acquisition module 10, in this embodiment, as part of a pixelated photon-counting detector 100 according to some embodiments of the present disclosure. The photon-counting data acquisition module may be part of, or include an ASIC, an electronic circuit, a processor and/or memory that execute one or more software or firmware programs, a combinational logical circuit, and/or other suitable components that provide the described functionality.

The photon-counting data acquisition module 10 comprises a signal input unit 12, one or, in this embodiment, more data acquisition channels 14a, 14b, 14c, also collectively referred to herein as data acquisition channels 14, and a signal output unit 16. The signal input unit 12 may comprise one or more signal inputs (not shown), each being adapted for receiving a train of pulses. For simplicity only three data acquisition channels 14a, 14b, 14c are shown in FIG. 1. The following discussion is also scalable to a large number of data acquisition channels. Each data acquisition channel 14 is adapted for converting at least one train of pulses 18, such as two trains of pulses 18a, 18b illustrated in FIGS. 8A and 8B, received from the signal input unit 12 to a counter signal. The signal output unit 16 is adapted for outputting the counter signal. Each data acquisition channel 14 comprises a pulse maximum identifier 20a, 20b, 20c, also collectively referred to herein as pulse maximum identifiers 20, and a discriminator/counter pair 22a, 22b, 22c comprising a discriminator 23 (see FIG. 5) and a counter 25 (see FIG. 5), also collectively referred to herein as discriminator/counter pairs 22.

Optionally, each data acquisition channel 14 may further comprise an analogue preprocessing chain 19a, 19b, 19c, also collectively referred to herein as analogue preprocessing chains 19. The analogue preprocessing chain 19 is configured to amplify and filter the at least one train of pulses 18. The analogue preprocessing chain 19 may comprise one or more charge-sensing amplifiers (CSA) and one or more pulse Shapers.

Figure 4:
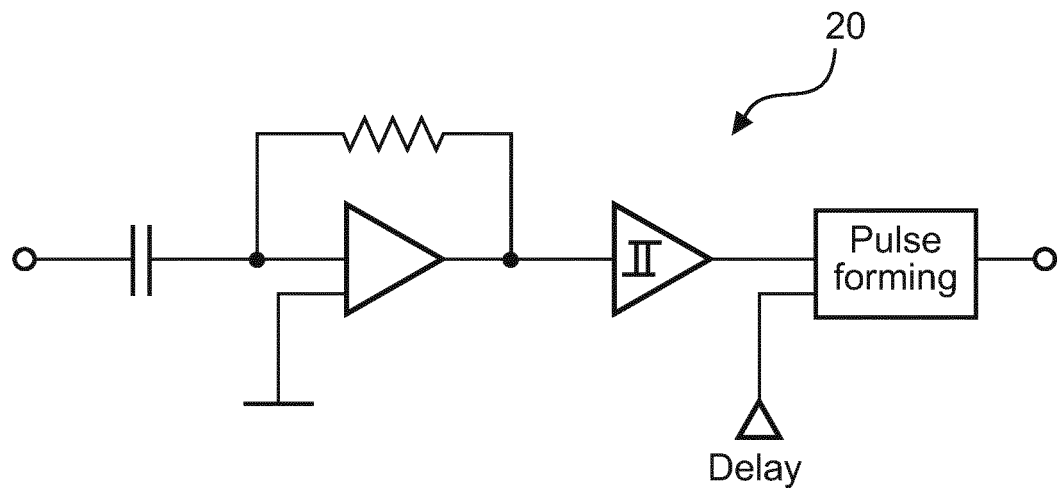
FIG. 4 shows schematically a pulse maximum identifier according to some embodiments of the present disclosure.
Figure 6A:
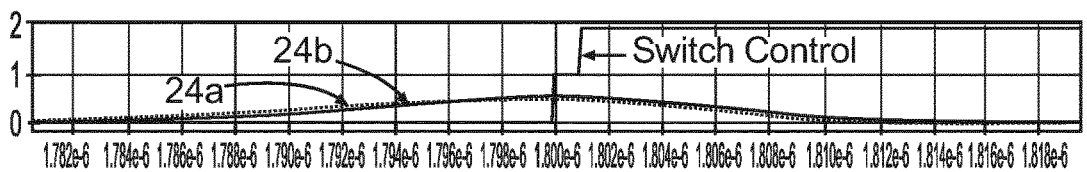
FIGS. 6A-6D show schematically two pulses representing two single events and corresponding outputs of a discriminator according to some embodiments of the present disclosure.
Figure 7A:
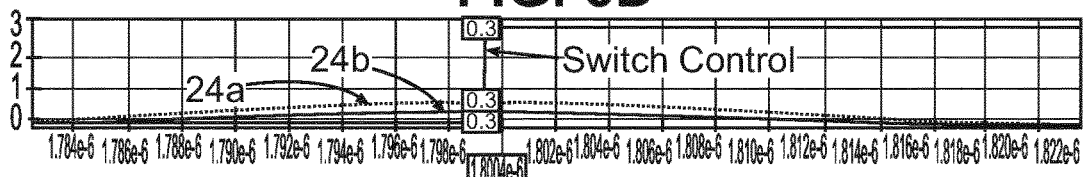
FIGS. 7A-7D show schematically two pulses representing a charge shared event and corresponding outputs of a discriminator according to some embodiments of the present disclosure.

The pulse maximum identifier 20 is configured to identify a maximum of a pulse 24, such as the pulse 24a, 24b illustrated in FIG. 6A and FIG. 7A, in the at least one received train of pulses 18. The pulse maximum identifier 20 may comprise a zero-crossing threshold preceded by a differentiator. A possible implementation is illustrated in FIG. 4.

Figure 5:
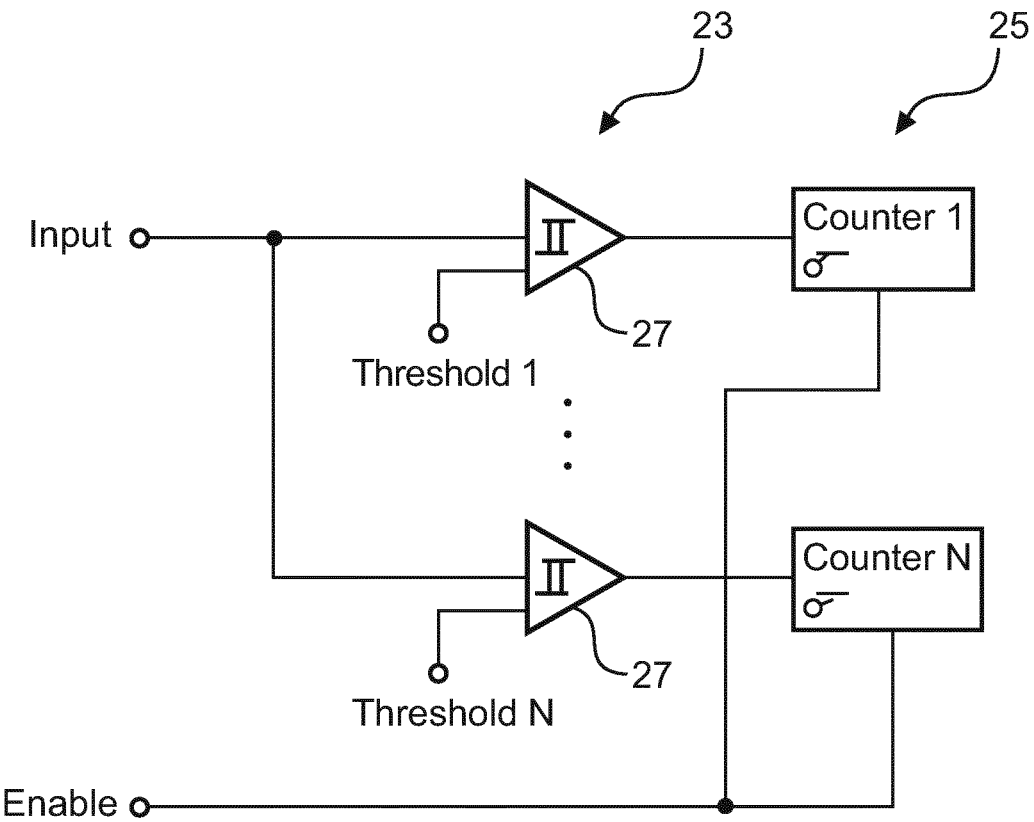
FIG. 5 shows schematically a discriminator according to some embodiments of the present disclosure.

The discriminator 23 is configured to be triggered, by a detection of a maximum of a pulse 24 in the at least one received train of pulses 18, to compare the pulse 24 with at least one signal threshold to generate the counter signal. As illustrated in FIG. 5, the discriminator 23 may comprise one or more comparators 27, each comparator 27 comparing the amplitude of the pulse 24 with one or more predetermined energy thresholds that correspond to one or more different energy ranges.

A counter 25 counts, for each energy range, a number of pulses that falls within the energy range based on the comparator output signals. The counter 25 may be enabled in response to a detection of a maximum of a pulse 24 to generate the counter signal; that is, the discriminator itself could be time continues but it is only allowed to increment the associated counters when enabled.

The pixelated photon-counting detector 100 comprises an array of pixels 110a, 110b, 110c, also collectively referred to as pixels 110. For simplicity, only three pixels are illustrated in FIG. 1. Each data acquisition channel 14a, 14b, 14c may be adapted for being connected to a corresponding pixel 110a, 110b, 110c of the pixelated photon-counting detector 100 to receive a train of pulses 18 indicative of an energy of photons incident on the respective pixel 110a, 110b, 110c of the pixelated photon-counting detector 100.

Figure 2:
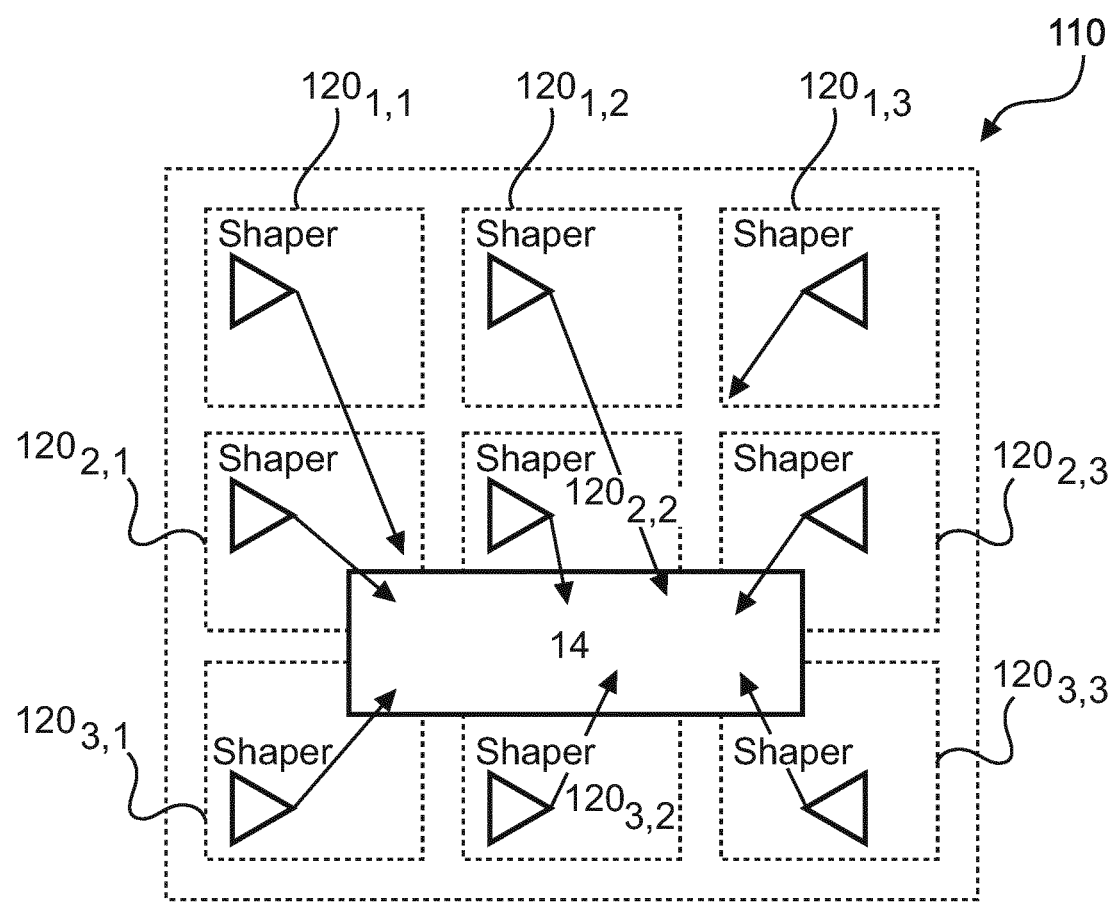
FIG. 2 shows schematically a 3×3 clustering of sub-pixels according to some embodiments of the present disclosure.

For example, the pixelated photon-counting detector 100 may be a semiconductor based photon-counting detector, which comprises two core components: semi-conductor material, such as Si, CdTe or CZT, with two electrodes, and photon-counting module 10 in form of read-out ASICs. When an incident X-ray photon interacts within the semi-conductor material, electrical charges i.e. electron-hole pairs, with an amount proportional to the deposited energy of the incident photon are produced and drifted towards the monolithic and pixelated electrodes separately under the influence of the externally applied electrical field. During the drifting process of electron-hole pairs, a transient current is generated and then processed by each connected data acquisition channel 14 through one optional analogue pre-processing chain 19, including one or more charge-sensitive preamplifier (not shown) and one or more pulse shapers as illustrated in FIG. 2, and the pulse maximum identifier 20 and the discriminator 23 with multiple pairs of voltage pulse height comparator and digital counter as illustrated in FIG. 5.

In some applications, techniques of sub-pixelation may be implemented. For example, US 2008/0329086 A1 describes clustering pixels using an anti-scatter grid. FIG. 2 shows a conceptual 3×3 clustering of sub-pixels $120_{N,M}$ representing a pixel 110, where N and M are positive integers. As illustrated in FIG. 2, the pulse shape may be adapted in a shaper (e.g., filter) of the optional analogue preprocessing chain 19 at the output of each sub-pixel $120_{N,M}$. Each data acquisition channel 14 is adapted for being connected to a cluster of sub-pixels $120_{N,M}$ of the pixelated photon-counting detector 100 to receive a plurality of trains of pulses 18, each indicative of an energy of photons incident on a respective sub-pixel $120_{N,M}$ of the cluster.

In some situations, it is noted that the spectral performance of the photon counting data acquisition module may be limited by a so-called charge-sharing effect, where charge, which is caused by a single photon, is shared between neighbouring sub-pixels. Charge sharing effect is almost unavoidable in photon counting detector because the radiation semi-conductor is electrically, rather than physically, pixelated. Charge sharing effect is more pronounced for small pixels, especially less than 0.5 mm.

Figure 3:
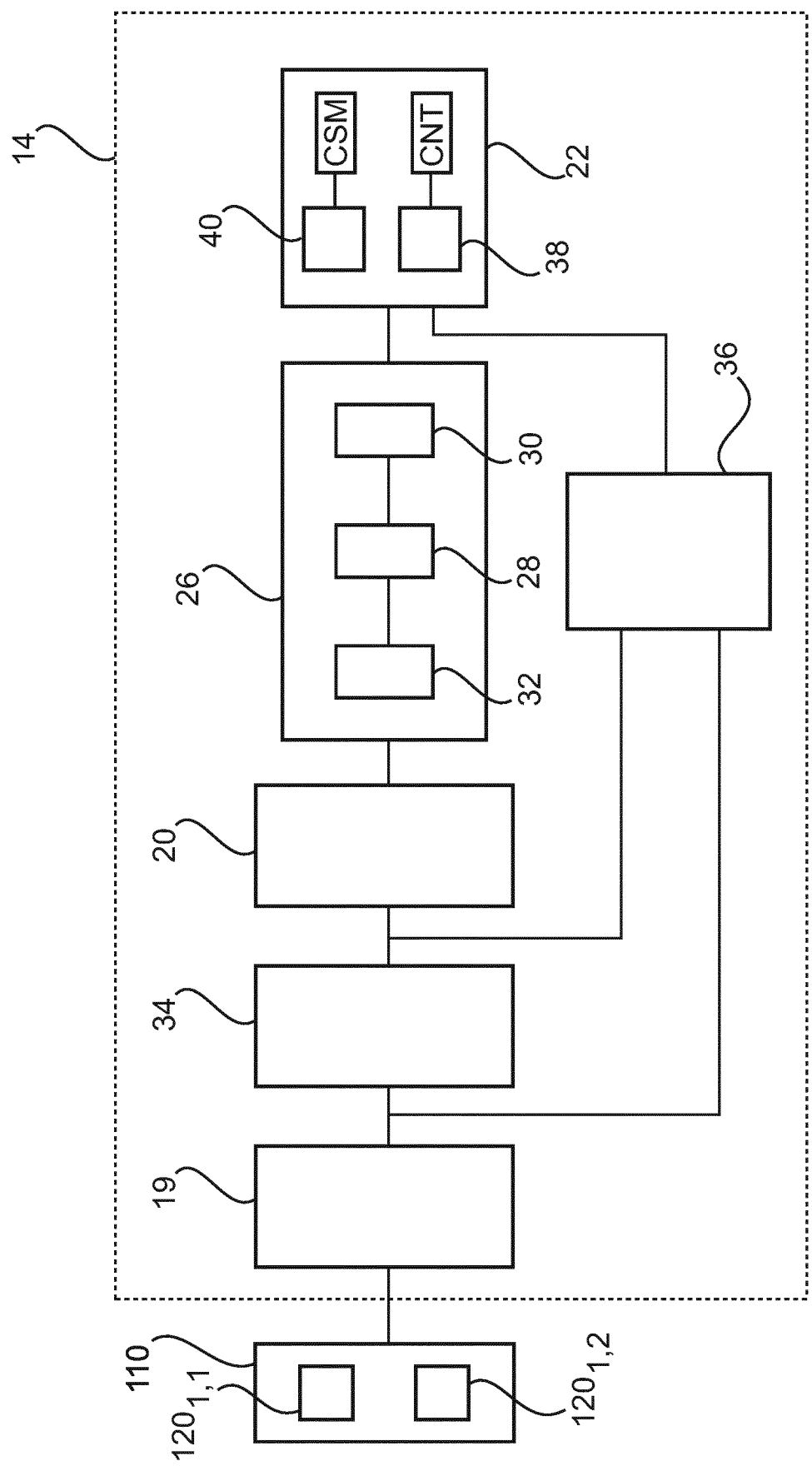
FIG. 3 shows schematically one data acquisition channel according to some embodiments of the present disclosure.

FIG. 3 shows a data acquisition channel 14 adapted for providing charge sharing compensation according to some embodiments of the present disclosure. For simplicity only two sub-pixels are illustrated, i.e. sub-pixel $120_{1,1}$ and sub-pixel $120_{1,2}$ representing a 1×2 clustering of sub-pixels. It is noted that the discussion and the model described hereafter is scalable to a large number of sub-pixels. No limitations other than noise and the digital complexity apply.

The at least one train of pulses 18 received from the signal input unit thus comprises a first train of pulses 18a and a second train of pulses 18b as illustrated in FIGS. 8A and 8B, each received from a respective sub-pixel $120_{1,1}$, $120_{1,2}$. The data acquisition channel 14 further comprises a selection logic 26.

In this embodiment, the pulse maximum identifier 20 is configured to identify maxima of a first pulse 24a in the first train of pulses 18a and a second pulse 24b in the second train of pulses 18b, as will be explained hereafter and particularly with respect to the exemplary embodiments in FIGS. 6 to 8. The first and second trains of pulses may be shaper outputs of the sub-pixels $120_{1,1}$, $120_{1,2}$. The pulse maximum identifier 20 may comprise a zero-crossing threshold preceded by a differentiator (or delay line summing). Its output goes high when a pulse has reached its maximum and it stays high for a pre-defined time. It may serve as coincidence logic. It is based on the fact that charge sharing across sub-pixels of a single event is instantaneous in nature. That is, both signal output units of the sub-pixels $120_{1,1}$ and $120_{1,2}$ must necessarily exhibit a maximum at the same time. The aforementioned delay may establish a coincidence window. The minimum window is set by the uncertainty in finding the maximum due to noise and circuits tolerances. A possible implementation of the pulse maximum identifier 20 (although other solutions may apply) is illustrated in FIG. 4. Turning back to FIG. 3, the selection logic 26 is configured to determine whether the maxima of the first pulse 24a and the second pulse 24b are within a coincidence window and to enable the discriminator to evaluate the first pulse 24a in the first train of pulses 18a or the second pulse 24b in the second train of pulses 18b directly if the first and second pulses are not within the coincidence window, or a sum of the first 24a and second pulses 24b if the first and second pulses are within the coincidence window. This will be explained hereafter and particularly with respect to the exemplary embodiments in FIGS. 6 to 8. In other words, the selection logic is configured to detect charge sharing events based on on-the fly coincidence detection and sum signals from sub-pixels of one cluster in the event of charge sharing. If no charge sharing event is detected, the signals from the sub-pixels are transmitted directly to the discriminator. This may allow charge sharing compensation based on on-the-fly coincidence detection and a time-discrete discriminator and thus allow an accurate decision of when to evaluate a shaper signal against energy thresholds.

An example of the selection logic 26 is illustrated in FIG. 3, although other solutions may apply. In this example, the selection logic 26 comprises a coincidence detector 28, a switch control 30, and a threshold sampling control 32.

The coincidence detector 28 is configured to evaluate a state of an output of the pulse maximum identifier 20 and to determine whether the first pulse 24a in the first train of pulses 18a, the second pulse 18b in the second train of pulses 18b, or both the first and second pulses are within the coincidence window. For example, it may indicate how many of the sub-pixels are active at the same time within the coincidence window. For example, a truth table may be used to decode which sub-pixel is active, for example, [0 0]→none, [0 1]→$120_{1,2}$, [1 0]→$120_{1,1}$, [1 1]→both.

The switch control 30 is configured to determine, based on the coincidence detector 28, whether to feedthrough the first pulse, the second pulse, or a sum of the first and second pulses to an input of the discriminator/counter pair 22. In other words, it takes decision on which signal is to be connected to the discriminator, i.e. which sub-pixel or if the sum of both.

The threshold sampling control 32 is configured to evaluate a state of an output of the pulse maximum identifier 20 and to trigger the discriminator 23 to perform comparison based on the evaluated state. In other words, the threshold sampling control 32 monitors the state of the shaper pulses and it enables the discriminator to evaluate a result accordingly. The output may remain high for a short time, e.g. 0.5 ns, or 2 ns, or 10 ns, depending on the count-rate performance and the noise requirements of the channel. This may work in the digital domain, i.e. the threshold counters may be allowed to increment or not.

To sum the signal, the data acquisition channel 14 may further comprise an adder 34 configured to add the first and second train of pulses. The adder 34 may work in an analogue summing mode. The adder 14 may comprise a high bandwidth amplifier with an input differential pair with N inverting input branches, where N is the number of sub-pixels of a cluster. Other implementation may consist on adding current branches of the shaper circuits.

In addition, the data acquisition channel 14 may further comprise a multiplexer 36, e.g. an analogue multiplexer, adapted for forwarding the first train of pulses, the second train of pulses, and a sum of the first and second trains of pulses to the discriminator in a time-multiplexed manner. In other words, the sub-pixels are clustered in a way that they share a set of energy thresholds. This is not energy staggering, the threshold system is time-multiplexed across all sub-pixels within a cluster. The input of the threshold system (every discriminator) is dependent on the decision on whether a given event is confined to a signal sub-pixel or charge shared across one or more neighbors. That is, for every signal photon a decision is made to feedthrough the shaper directly to the discriminator or to take the signal from a shaper summing mode which is continuously available. The multiplexer 36 may take the result from the switch control 30 and accordingly connect the required signal to the discriminator 23. For overall pile-up requirements, it may be beneficial to have a high-speed multiplexer. Propagation delays may be added to all signals if required.

The discriminator/counter pair 22 may comprise at least one threshold 38 and a charge-sharing counter 40. The at least one threshold 38 may be conventional discriminators and counters. The counters are, however, only allowed to increment their values at given time interval, i.e. when the decision of which signal needs to be evaluated is available. A simple enable bit in the digital counters may suffice to enforce this functionality. FIG. 7 shows an exemplary implementation. The charge-sharing counter 40 is adapted for being triggered by a detection of the maxima of the first pulse and the second pulse within a coincidence window to increase a value. In other words, the control signals commandeering the decisions can also be used to output a count value representative of how many events have been treated as charge shared. This may also be proven valuable in determining pile-up corrections.

To illustrate the working principle of the photon-counting data acquisition module 10, FIGS. 6A-6D illustrate the simulation results of a single event that is not shared across two sub-pixels. For simulation purposes both sub-pixels $120_{1,1}$ and $120_{1,2}$ as illustrated in FIG. 3 provide the same train of pulses, however, with a time delay with respect to each other. In this case, the time delay is set to only 1 ns. The simulation shows cases with the capability of distinguishing pulses that are considered single events in a very short time interval, allowing accommodating very high counting rates.

As illustrated in FIG. 6A, both sub-pixels $120_{1,1}$ and $120_{1,2}$ are processing two unrelated single events. The first pulse 24a indicative an energy of photons incident on the sub-pixel $120_{1,1}$ and the second pulse 24b indicative of an energy of photons incident on the sub-pixel $120_{1,2}$ are only 1 ns apart, both having 60 keV energy (0.6 in the simulation). The switch control 30 indicates that the first sub-pixel $120_{1,1}$ is active with an output of "1" and shortly after that a second sub-pixel $120_{1,2}$ is also active with an output "2". Since the maxima is not located within a predefined coincidence window of 0.5 ns, the switch control does not indicate the presence of charge sharing with an output of "3".

Figure 6B:
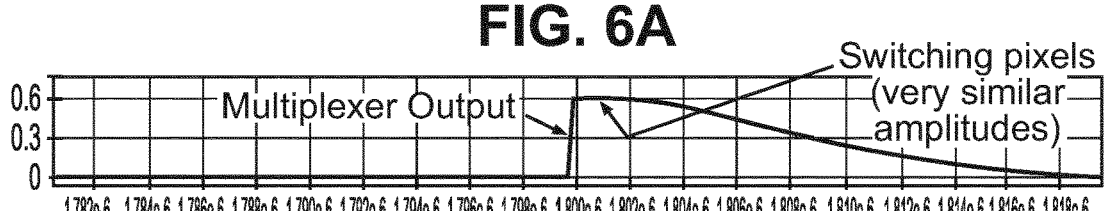

In FIG. 6B, the multiplexer 34 directs the output of the sub-pixel $120_{1,1}$ to the input of the discriminator 23 in a first instance. Shortly afterwards the output of the sub-pixel $120_{1,2}$ is directed towards the discriminator 23. The change in the selection is not observable in FIG. 6B due to both signals having very similar values.

Figure 6C:
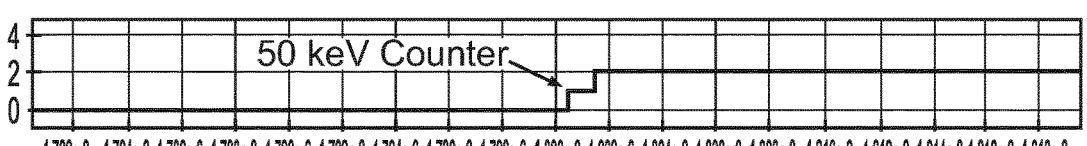

In FIG. 6C, the at least one threshold 36 of the discriminator 23 is accordingly enabled twice, once for each pulse, such that the sub-pixel $120_{1,1}$ is evaluated and immediately thereafter the sub-pixel $120_{1,2}$ is assessed.

Figure 6D:
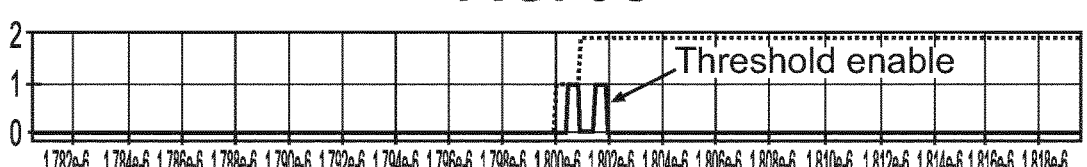

In FIG. 6D, the lowest threshold, which is set to 50 keV, registers two counts, adequately representing the arrival of two independent signal events on two sub-pixels $120_{1,1}$ and $120_{1,2}$.

FIGS. 7A-7D illustrate the simulation results of a single event that is shared across two sub-pixels. In this case, both sub-pixels $120_{1,1}$ and $120_{1,2}$ again have the same train of pulses, however, with no delay. This serves the purpose to simulate the correct attribution of the charge sharing compensation mechanism. The output the sub-pixel $120_{1,2}$ is also scaled by 50%, which entails that a single 90 keV event is split into two smaller events and the sub-pixel $120_{1,2}$ receives the remaining 30 keV.

In FIG. 7A, as mentioned above, the sub-pixel $120_{1,1}$ exhibits a 60 keV event, while the sub-pixel $120_{1,2}$ exhibits 30 keV. Since both maxima are found to occur within the coincidence window of 0.5 ns, the switch control 30 indicates with "3" that both signals have to be regarded as a single charge shared event.

Figure 7B:
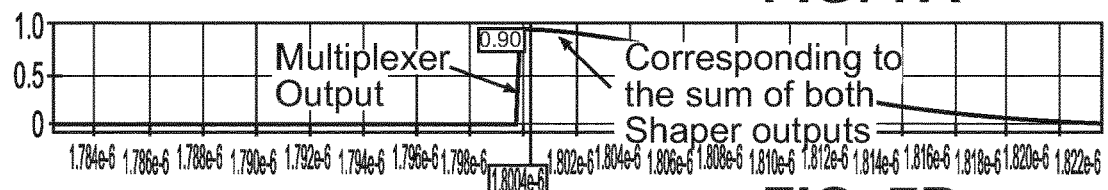

Accordingly, as shown in FIG. 7B, the multiplexer 36 directs the addition of both signals to the discriminator input, showing a total energy of 90 keV (0.9 in the simulation).

Figure 7C:
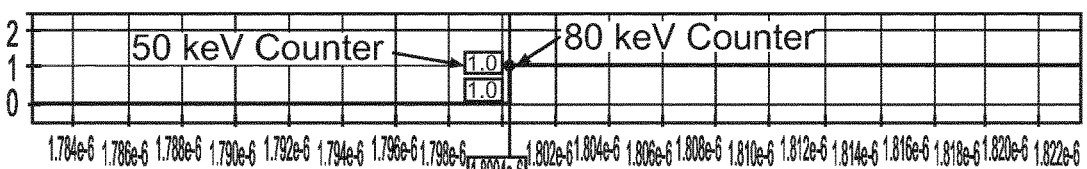

In FIG. 7C, the at least one threshold 36 of the discriminator 23 is accordingly enabled once, such that the sum of both signals is evaluated.

Figure 7D:
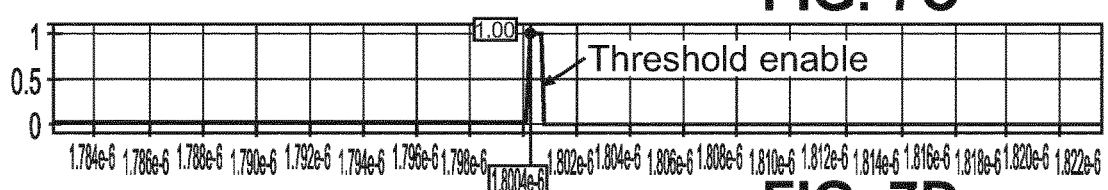

In FIG. 7D, since the total energy is 90 keV, both 50 keV and 80 keV thresholds are incremented only once, representing the arrival of a single event that is registered on both sub-pixels $120_{1,1}$ and $120_{1,2}$.

FIGS. 8A to 8D illustrate the simulation results of multiple events with a mixture of single events and charge shared events. As illustrated in FIGS. 8A and 8B, in this simulation, each sub-pixel $120_{1,1}$ and $120_{1,2}$ has a unique train of pulses 18a, 18b, monochromatic at 60 keV. A third independent train of pulses generated and split across both sub-pixels, mimicking charge sharing events in both trains of pulses 18a, 18b. In this simulation, the sub-pixel $120_{1,1}$ receives 60% of the charge, i.e. 36 keV and the sub-pixel and $120_{1,2}$ 40%, i.e. 24 keV. All events have 60 keV. Therefore, if the model behaves as expected, the 50 keV threshold should count as many events as there were in the third independent pulse trains combined (if no pile-up). In particular, the first train of pulses 18a has a total of nineteen events in 30 μs. The second train of pulses 18b has a total of fourteen events. The third train of pulses, mimicking charge sharing events, has a total of seven single events, shared across both sub-pixels $120_{1,1}$ and $120_{1,2}$, i.e. seven smaller events each.

As can be seen in FIG. 8C, the 50 keV threshold 36 adequately identifies 40 events.

As can be seen in FIG. 8D, the charge-sharing counter 38 also identifies correctly the seven events that are shared across the sub-pixels. The position of the second cursor shows how despite having occurred a total of seven shaper pulses, only six were counted, including five single events and one charge share event split across pixels.

Figure 9:
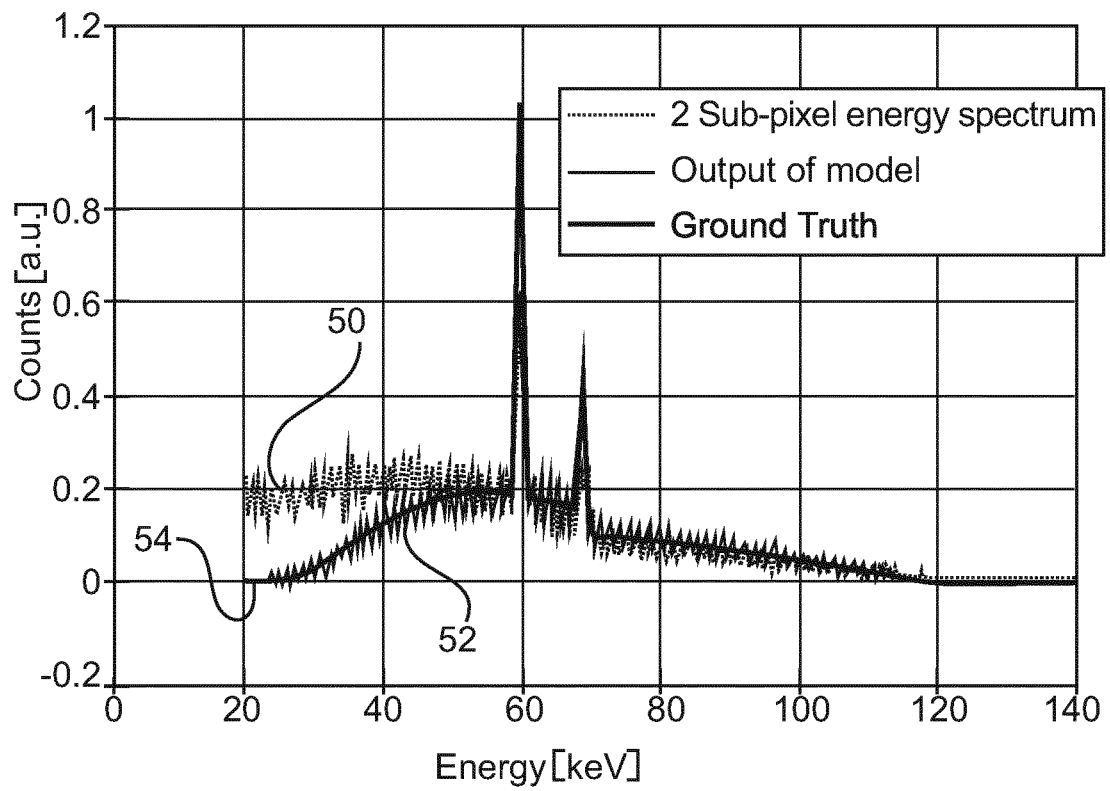
FIG. 9 shows schematically an impact of charge sharing on tube spectrum and the correction according to some embodiments of the present disclosure.

FIG. 9 shows a count-rate simulation using a polychromatic tube spectrum illustrating a two sub-pixel energy spectrum 50, an output of the model 52, and a ground truth 54. To facilitate the interpretation, a low rate of 0.5 Mcps has been used to ensure that there is no pile-up. The benefit of using the model may become more obvious with the resulting registered spectrum falling on top of the ground truth 54. In this simulation it is intended to show the resulting observed count-rate as a function of subsequently increasing incident count rate. In view of execution time, this simulation has been restricted to 20 Monte Carlo realizations for each incident count rate point. The tube spectrum has been used for this simulation.

Figure 10:
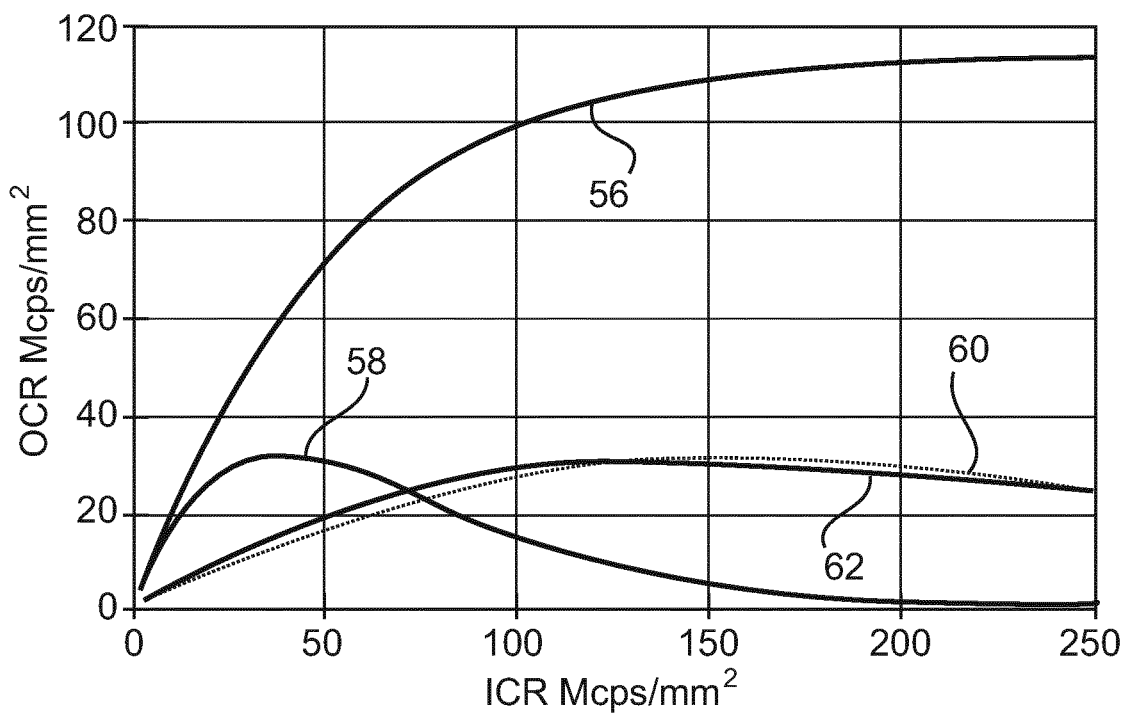
FIG. 10 shows schematically a pile-up curve according to some embodiments of the present disclosure.

FIG. 10 shows the results of this simulation for a 30 keV threshold. Four traces are shown:
i) Model Output 56: the result of feeding the model with the described trains of pulses. It shows a non-paralyzable characteristic.
ii) Equivalent 1×2 sub-pixel 58: it shows the rate curve for a larger equivalent sub-pixel, i.e. it serves as comparison. The model and this graphs serve the same equivalent area.
iii) Sub-pixel with charge sharing 60: The train of pulses of one sub-pixel with additional charge sharing form a neighbor sub-pixel.
iv) Sub-pixel without charge sharing 62: The train of pulses of one of the sub-pixels before any charge sharing has been added.

Figure 11:
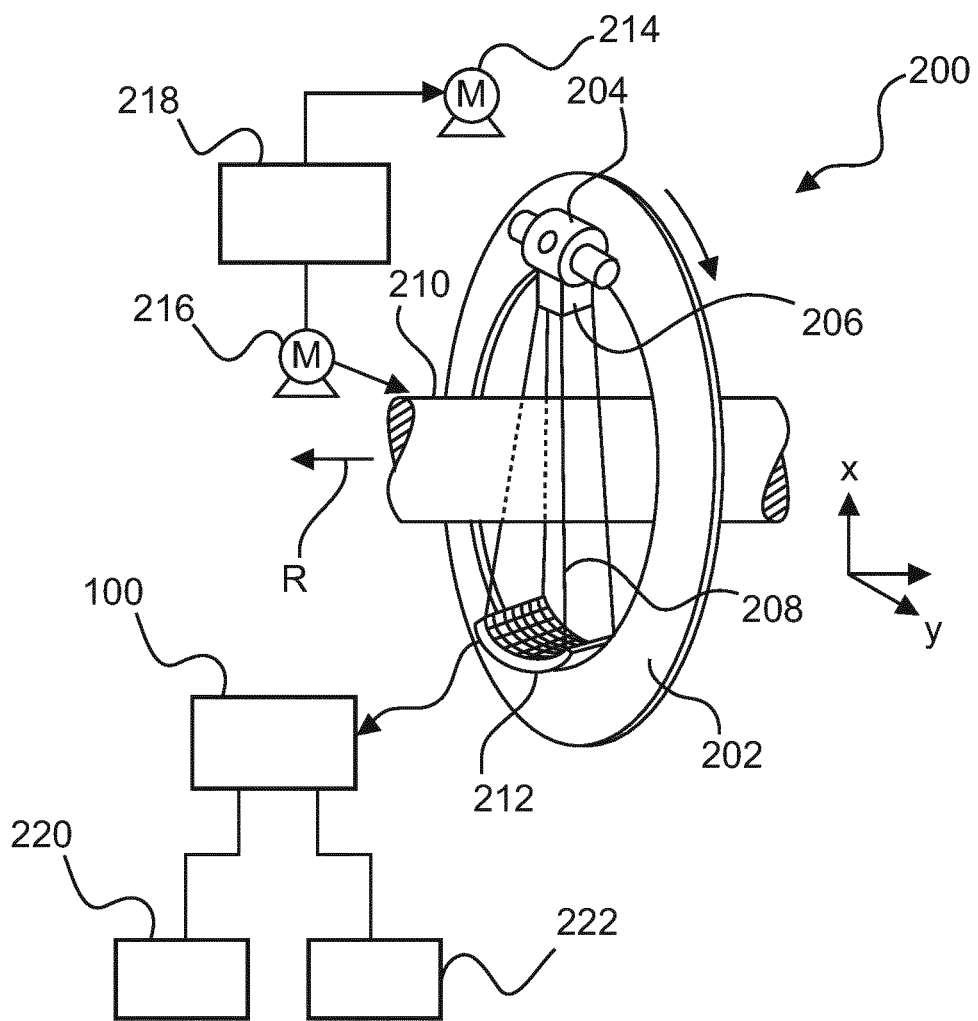
FIG. 11 shows schematically an imaging system for generating an image of an object according to some embodiments of the present disclosure.

The pixelated photon-counting detector 100 may be at least one of an X-ray detector, a gamma ray detector and a fluorescence detector. A possible implementation of the pixelated photon-counting detector 100 may be in an imaging system 200 such as a computed tomography CT scanner schematically illustrated in FIG. 11. The imaging system 200 includes a gantry 202, which is capable of rotation about a rotational axis R, which extends parallel to a z direction. A radiation source 204, which in this embodiment is an x-ray tube, is mounted on the gantry 202 and is provided with a collimator 206, which forms a conical radiation beam 208 from the radiation generated by the radiation source 204. The radiation traverses the object being, in this embodiment, a human patient within a cylindrical examination zone 210 and hence the patient. The radiation beam 208 is incident on a photon-counting detector 100, which is mounted on the gantry 202. The pixelated photon-counting detector 100 may have a one or two-dimensional array of pixels 110, which are connected to a photon-counting data acquisition module 10 to count individual photons incident on the pixels 110. Since the discriminators are allowed to evaluate signals only in discrete time intervals, the system is inherently non-paralyzable in the sense that the observed count rate increases moronically with the input count rate. In some embodiments, each pixel 110 may be a cluster of sub-pixels 120, the photon-counting data acquisition module 10 may be configured to count individual photons incident on the sub-pixels 120 of a cluster and to provide charge sharing compensation.

The imaging system 200 comprises two motors 214, 216. The gantry 202 is driven at a preferably constant but adjustable angular speed by the motor 214. The motor 216 is provided for displacing the patient, who is arrange on a patient table, in the examination zone 210 parallel to the direction of the rotational axis R or the z axis. The motors 214, 216 are controlled by a control unit 218, for instance, such that the radiation source 204 and the patient within the examination zone 210 move relative to each other along a helical trajectory. However, it is also possible that the radiation source 204 and the patient move relatively to each other along another trajectory. For instance, in an embodiment, the radiation source 204 may move around the patient along a circular trajectory.

The imaging system 200 may further comprise an input unit 220 like a keyboard, a computer mouse, a touch pad, etc., and a display 222. The input unit 220 may be adapted to allow a user to input a clustering input defining a desired clustering of the pixels. The photon counting data acquisition module 10 of the pixelated photon-counting detector 100 may be adapted to consider the desired clustering defined by the clustering input while determining the charge-sharing-photon count for a macro pixel. The input unit 220 may be adapted to allow for changes in software and/or hardware configurations, in order to amend the clustering, especially the size of the clusters.

Figure 12:
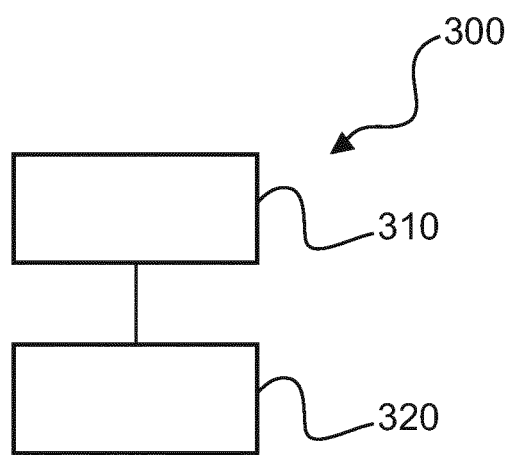
FIG. 12 shows schematically a flowchart illustrating a method according to some embodiments of the present disclosure.

FIG. 12 shows a flow diagram of a method 300 for photon counting. In step 310, a maximum of a pulse in at least one received train of pulses is identified with a pulse maximum identifier. In step 320, a discriminator is triggered by a detection of a maximum of a pulse in the at least one received train of pulses, to compare the pulse with at least one signal threshold. Alternatively, in step 320, a counter is enabled, in response to a detection of a maximum of a pulse in the at least one received train of pulses, to generate the counter signal Optionally, the at least one received train of pulses are indicative of an energy of photons incident on a respective pixel or a respective cluster of sub-pixels of a pixelated photon-counting detector.

The method 300 may comprise further steps. In an option, the at least one received train of pulses comprises a first train of pulses and a second train of pulses. The method further comprises identifying maxima of a first pulse in the first train of pulses and a second pulse in the second train of pulses, determining whether the maxima of the first pulse and the second pulse are within a coincidence window, and evaluating the first pulse in the first train of pulses, the second pulse in the second train of pulses, or a sum of the first pulse and the second pulse based on the determination results.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A photon-counting data acquisition module, comprising:
   a signal input unit;
   one or more data acquisition channels, each channel adapted for converting at least a first train of pulses from a first sub-pixel and a second train of pulses from a second sub-pixel, received from the signal input unit, to a counter signal; and
   a signal output unit adapted for outputting the counter signal;
      wherein each data acquisition channel comprises a pulse maximum identifier and a discriminator/counter pair comprising a discriminator and a counter;
      wherein the pulse maximum identifier is configured to identify a maximum of a first pulse in the first received train of pulses and a second pulse in the second received train of pulses;
      wherein the discriminator is configured to be triggered, by a detection of a maximum of a pulse in the at least first and second received trains of pulses, to compare the pulse with at least one signal threshold to generate the counter signal, wherein the counter is configured to be enabled in response to a detection of a maximum of a pulse in the at least first and second received trains of pulses to generate the counter signal;
   a selection logic configured to determine whether the maxima of the first pulse and the second pulse are within a coincidence window and to enable the discriminator to evaluate the first pulse in the first train of pulses or the second pulse in the second train of pulses directly if the first and second pulses are not within the coincidence window, or a sum of the first and second pulses if the maxima of the first and second pulses are within the coincidence window.

2. The device according to claim 1, wherein the selection logic comprises:
   a coincidence detector;
   a switch control; and
   a threshold sampling control;
      wherein the coincidence detector is configured to evaluate a state of an output of the pulse maximum identifier and to determine whether the first pulse in the first train of pulses, the second pulse in the second train of pulses, or both the first and second pulses are within the coincidence window;
      wherein the switch control is configured to determine, based on the evaluation and determination of the coincidence detector, whether to feedthrough the first pulse, the second pulse or a sum of the first and second pulses to an input of the discriminator; and
      wherein the threshold sampling control is configured to evaluate a state of an output of the pulse maximum identifier and to trigger the discriminator to perform comparison based on the evaluated state.

3. The device according to claim 1, wherein data acquisition channel further comprises:
   an adder configured to add the first and second train of pulses.

4. The device according to claim 1, wherein the data acquisition channel further comprises:
   a multiplexer adapted for forwarding the first train of pulses, the second train of pulses, and a sum of the first and second trains of pulses to the discriminator in a time-multiplexed manner.

5. The device according to claim 1, wherein the discriminator/counter pair further comprises:
   a charge-sharing counter adapted for being triggered by a detection of the maxima of the first pulse and the second pulse within a coincidence window to increase a value.

6. A pixelated photon-counting detector, comprising:
   an array of pixels, each pixel comprising a cluster of sub-pixels; and
   a photon-counting data acquisition device according to claim 1;
   wherein each data acquisition channel of the photon-counting data acquisition device is configured to receive at least two trains of pulses, each train indicative of an energy of photons incident on a respective sub-pixel of the pixelated photon-counting detector.

7. The detector according to claim 6, wherein the pixelated photon-counting detector is at least one of an X-ray detector, a gamma ray detector, and a fluorescence detector.

8. A method (300) for photon counting, comprising:
   identifying, with a first pulse maximum identifier, a maximum of a first pulse in a first received train of pulses from a first sub-pixel and with a second pulse maximum identifier, a maximum of a second pulse in a second received train of pulses from a second first sub-pixel;
   triggering a discriminator, by a detection of a maximum of a pulse in at least one of the at least first and second received trains of pulses, to compare the pulse with at least one signal threshold;
   enabling a counter, in response to a detection of a maximum of a pulse in the at least first and second received trains of pulses, to generate the counter signal; and
   determining whether the maxima of the first and second trains of pulses are within a coincidence window; and
   evaluating the first pulse in the first train of pulses, the second pulse in the second train of pulses, or a sum of the first pulse and the second pulse based on the determination result.

9. A non-transitory computer-readable medium for storing executable instructions that, when executed, cause the method of claim 8 to be performed.

* * * * *